(12) United States Patent
Smith et al.

(10) Patent No.: US 8,298,137 B2
(45) Date of Patent: Oct. 30, 2012

(54) METHOD FOR TRANSMITTING TORQUE AND VARIABLY FLEXING A CORRUGATED INSERTION DEVICE

(75) Inventors: Kevin W. Smith, Coral Gables, FL (US); Derek Dee Deville, Miami, FL (US); Korey Kline, Miami, FL (US); Matthew A. Palmer, Miami, FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 13/006,760

(22) Filed: Jan. 14, 2011

(65) Prior Publication Data

US 2011/0130630 A1   Jun. 2, 2011

Related U.S. Application Data

(62) Division of application No. 12/432,351, filed on Apr. 29, 2009, now Pat. No. 7,914,445, which is a division of application No. 11/502,322, filed on Aug. 10, 2006, now Pat. No. 7,988,621.

(51) Int. Cl.
*A61B 1/01* (2006.01)

(52) U.S. Cl. ...................................... 600/149

(58) Field of Classification Search .......... 604/187, 604/95.04, 523; 600/146, 144, 139, 114, 600/149
See application file for complete search history.

(56) References Cited

U.S. PATENT DOCUMENTS

| | | | |
|---|---|---|---|
| 3,557,780 A | 1/1971 | Sato | |
| 3,998,216 A | 12/1976 | Hosono | |
| 4,176,662 A | 12/1979 | Frazer | |
| 4,575,185 A | 3/1986 | Wentzell et al. | |
| 4,753,223 A | 6/1988 | Bremer | |
| 4,762,118 A | 8/1988 | Lia et al. | |
| 4,815,450 A | 3/1989 | Patel | |
| 4,817,613 A * | 4/1989 | Jaraczewski et al. | ......... 600/435 |
| 4,838,859 A | 6/1989 | Strassman | |
| 4,890,602 A | 1/1990 | Hake | |
| 4,893,613 A | 1/1990 | Hake | |
| 4,998,282 A | 3/1991 | Shishido et al. | |

(Continued)

FOREIGN PATENT DOCUMENTS

WO   2005048814 A2   6/2005

OTHER PUBLICATIONS

International Search Report for PCT/US08/064084 dated Dec. 9, 2008.

(Continued)

*Primary Examiner* — Kevin C Sirmons
*Assistant Examiner* — Michael J Anderson
(74) *Attorney, Agent, or Firm* — Mayback & Hoffman, P.A.; Gregory L. Mayback; Rebecca A. Tie

(57) ABSTRACT

A method for transmitting torque and variably flexing an insertion device for receiving an instrument includes the steps of providing a hollow body, transmitting torque along the hollow body with a corrugated tube, applying suction to create a vacuum in the hollow body for placing the hollow body in a relatively stiff condition, relieving the vacuum for placing the hollow body in a relatively flexible condition, maintaining the hollow body in the relatively flexible and relatively stiff conditions with tendons disposed within the hollow body, and individually adjusting at least some of the tendons in length for steering a distal end of the hollow body.

16 Claims, 16 Drawing Sheets

U.S. PATENT DOCUMENTS

| | | | |
|---|---|---|---|
| 5,211,633 A | 5/1993 | Stouder, Jr. | |
| D337,733 S | 7/1993 | Ewing et al. | |
| 5,259,366 A | 11/1993 | Reydel et al. | |
| 5,337,733 A | 8/1994 | Bauerfeind et al. | |
| 5,386,817 A | 2/1995 | Jones | |
| 5,577,992 A | 11/1996 | Chiba et al. | |
| 5,759,151 A | 6/1998 | Sturges | |
| 5,807,237 A | 9/1998 | Tindel | |
| 5,873,816 A | 2/1999 | Kagawa et al. | |
| 6,117,068 A | 9/2000 | Gourley | |
| 6,196,967 B1 | 3/2001 | Lim | |
| 6,346,077 B1 | 2/2002 | Taylor | |
| 6,375,654 B1 | 4/2002 | McIntyre | |
| 6,387,044 B1 | 5/2002 | Tachibana | |
| 6,468,203 B2 | 10/2002 | Belson | |
| 6,478,731 B2 | 11/2002 | Speier | |
| 6,506,150 B1 | 1/2003 | Ouchi | |
| 6,517,477 B1 | 2/2003 | Wenlandt | |
| 6,610,007 B2 | 8/2003 | Belson et al. | |
| 6,645,223 B2 | 11/2003 | Boyle et al. | |
| 6,800,056 B2 | 10/2004 | Tartaglia et al. | |
| 6,802,809 B2* | 10/2004 | Okada | 600/146 |
| 6,858,005 B2* | 2/2005 | Ohline et al. | 600/141 |
| 6,942,613 B2 | 9/2005 | Ewers et al. | |
| 6,974,411 B2* | 12/2005 | Belson | 600/114 |
| 6,984,203 B2 | 1/2006 | Tartaglia et al. | |
| 7,066,880 B2 | 6/2006 | Wendlandt | |
| 7,104,951 B2 | 9/2006 | Hasegawa et al. | |
| 7,435,214 B2 | 10/2008 | Kucklick | |
| 7,811,228 B2 | 10/2010 | Adams | |
| 2002/0002323 A1* | 1/2002 | Moriyama | 600/140 |
| 2002/0177750 A1 | 11/2002 | Pilvisto | |
| 2003/0135198 A1 | 7/2003 | Berhow et al. | |
| 2004/0044350 A1 | 3/2004 | Martin | |
| 2004/0138529 A1* | 7/2004 | Wiltshire et al. | 600/144 |
| 2004/0182393 A1 | 9/2004 | MacMillan | |
| 2004/0186350 A1 | 9/2004 | Brennenman et al. | |
| 2005/0075538 A1* | 4/2005 | Banik et al. | 600/141 |
| 2005/0131279 A1* | 6/2005 | Boulais et al. | 600/141 |
| 2006/0025652 A1 | 2/2006 | Vargas | |
| 2006/0069346 A1* | 3/2006 | Smith et al. | 604/95.05 |
| 2007/0088367 A1 | 4/2007 | Von Weymarn-Scharli | |
| 2007/0179339 A1 | 8/2007 | Gorini et al. | |
| 2007/0208300 A1 | 9/2007 | Pravong et al. | |
| 2007/0270648 A1 | 11/2007 | Smith | |
| 2008/0091170 A1* | 4/2008 | Vargas et al. | 604/528 |
| 2009/0149710 A1 | 6/2009 | Stefanchik | |

OTHER PUBLICATIONS

International Search Report for PCT/US/068348 dated Oct. 30, 2008.
ASGE Abstract 136: "A Split Overtube for Easier Colonoscopy" (author not named).
International Search Report for PCT/US07/012179 dated Sep. 12, 2008.
International Search Report for PCT/US07/05478 dated Dec. 17, 2007.
International Search Report for PCT/US07/075701 dated Aug. 29, 2008.

* cited by examiner

METHOD FOR TRANSMITTING TORQUE AND VARIABLY FLEXING A CORRUGATED INSERTION DEVICE

CROSS-REFERENCE TO RELATED APPLICATION

This application is:
a divisional of U.S. patent application Ser. No. 12/432,351, filed on Apr. 29, 2009;
a divisional of U.S. patent application Ser. No. 11/502,322, filed on Aug. 10, 2006;
and
a divisional of U.S. patent application Ser. No. 13/006,745, filed concurrently herewith,
the entire disclosures of which are hereby incorporated herein by reference in their entireties.

STATEMENT REGARDING FEDERALLY SPONSORED RESEARCH OR DEVELOPMENT

Not applicable.

BACKGROUND OF THE INVENTION

1. Field of the Invention

The invention relates to a torque-transmitting, variably-flexible, corrugated insertion device. The invention also relates to a method for transmitting torque and variably flexing a corrugated insertion device.

2. Description of the Related Art

Prior art insertion devices of this general type have been quite complicated, cumbersome and difficult to use. Such devices have a relatively large diameter, a limited maximum length, a limited transmission of torque and present obstacles to insertion of instruments.

SUMMARY OF THE INVENTION

It is accordingly an object of the invention to provide a torque-transmitting, variably-flexible, corrugated insertion device and a method for transmitting torque and variably flexing a corrugated insertion device, which overcome the hereinafore-mentioned disadvantages of the heretofore-known devices and methods of this general type and which are simpler to construct, have a smaller diameter, a greater torque transmission, may be made longer and allow smooth insertion of an instrument.

With the foregoing and other objects in view there is provided, in accordance with the invention, a method for transmitting torque and variably flexing an insertion device for receiving an instrument including the steps of providing a hollow body, transmitting torque along the hollow body with a corrugated tube, applying suction to create a vacuum in the hollow body for placing the hollow body in a relatively stiff condition; relieving the vacuum for placing the hollow body in a relatively flexible condition, maintaining the hollow body in the relatively flexible and relatively stiff conditions with tendons disposed within the hollow body, and individually adjusting at least some of the tendons in length for steering a distal end of the hollow body.

The corrugated tube supports the insertion device and maintains a tubular shape, without the need for a support spring. Therefore, the insertion device has a narrower diameter, may have a longer length, such as 50 inches or longer, transmits greater torque than a spring and does not impair the insertion of an instrument in contrast to a spring.

In accordance with another feature of the invention, there is provided an inner liner within the corrugated tube for preventing vacuum leakage and aiding in insertion of the instrument. The liner may be adhesively connected to the corrugated tube.

In accordance with a further feature of the invention, there are provided tendons within the hollow body for maintaining the hollow body in the relatively flexible and relatively stiff conditions. In a steerable embodiment of the device, some of the tendons are individually adjustable in length for steering the distal end of the hollow body. The tendons and the corrugated tube are at least partly disposed between an outer jacket and an inner sleeve where the transitioning device, such as a vacuum connection, applies suction for frictionally locking the tendons and the corrugated tube in place.

In accordance with an added feature of the invention, inner and outer handles of the hollow body define a vacuum plenum volume therebetween communicating between the outer jacket and the inner sleeve and with a vacuum port. A sliding valve encircles the outer handle and has a vacuum inlet/outlet for communicating with the vacuum connection. The sliding valve slides between a position in which the vacuum inlet/outlet communicates with the vacuum port and a position in which the vacuum inlet/outlet is sealed against the vacuum port. The sliding valve has a recessed O-ring for sealing the sliding valve to the outer handle. This provides a convenient way for the operator of the device to adjust the stiffness while manipulating the device.

In accordance with an additional feature of the invention, the tendons extend substantially entirely over a flexible section of the hollow body beyond the handle. The tendons float in the handle when the hollow body is in the relatively flexible condition. The tendons are not in tension or compression when the hollow body is in both the relatively flexible and relatively stiff conditions. The tendons are rigidly attached at the distal end and allowed to float at the handle. In this regard, there is provided a termination bushing at the distal end to which at least some of the tendons are attached. Each two of the tendons form legs of a U-shaped configuration passing through holes in the termination bushing and being interconnected by a crosspiece extending between two of the holes distally of the termination bushing, like a large staple. This avoids the need to weld the tendons in place at the distal end and removes the danger of welds breaking at the distal end. The tendons include steering tendons attached to the termination bushing and non-steering tendons attached to one of the vertebrae.

In accordance with yet another feature of the invention, the tendons vary in number along the hollow body for providing zones of varying stiffness. The number of tendons may be greater toward the distal end than toward the proximal end for increasing stiffness at the distal end.

In accordance with yet another feature of the invention, there are provided knobs each sliding in a respective slot formed in the handle. The individually adjustable tendons are each steering tendons connected to a respective one of the knobs for steering the distal end. This allows the operator of the device to easily steer the distal end in any direction.

In accordance with yet another feature of the invention, the corrugated tube has at least one cuffed end. The cuffed end or ends prevent vacuum leakage and thus preserve stiffness, when required.

In accordance with yet a further feature of the invention, vertebrae are disposed along the corrugated tube for guiding the tendons. The vertebrae may be disposed between corrugation peaks of the corrugated tube and may be elastic and have a parting line to be opened into a gap for snapping the vertebrae onto the corrugated tube. At least some of the vertebrae have channels formed therein permitting movement of at least some of the tendons therethrough.

In accordance with another mode of the invention, there is provided the step of preventing vacuum leakage and aiding in insertion of the instrument with a liner disposed within the corrugated tube.

In accordance with a further mode of the invention, there is provided the step of adhesively connecting the liner to the corrugated tube.

In accordance with an added mode of the invention, there is provided the step of providing the hollow body with an outer jacket and an inner sleeve, providing the tendons at least partly between the outer jacket and the inner sleeve, providing the corrugated tube between the outer jacket and the inner sleeve, and carrying out the step of applying suction between the outer jacket and the inner sleeve with a transitioning device for frictionally locking the tendons and the corrugated tube in place.

In accordance with yet another mode of the invention, there is provided the step of individually adjusting at least some of the tendons as steering tendons with knobs each connected to a respective one of the steering tendons and each sliding in a respective slot formed in a handle at a proximal end of the hollow body.

In accordance with yet an added mode of the invention, there is provided the step of providing a vacuum connection as the transitioning device, and actuating the vacuum connection with a valve at the handle.

In accordance with yet an additional mode of the invention, there is provided the step of guiding the tendons with vertebrae disposed along the corrugated tube.

In accordance with again another mode of the invention, there is provided the step of placing the vertebrae between corrugation peaks of the corrugated tube for guiding the tendons.

In accordance with again a further mode of the invention, there is provided the step of snapping the vertebrae onto the corrugated tube by elastically opening the vertebrae at a parting line into a gap.

In accordance with again an added mode of the invention, there is provided the step of permitting movement of at least some of the tendons through channels formed in at least some of the vertebrae.

In accordance with again an additional mode of the invention, there is provided the step of attaching at least some of the tendons to a termination bushing at a distal end of the hollow body.

In accordance with still another mode of the invention, there is provided the step of forming each two of the tendons into legs of a U-shaped configuration passing through holes in the termination bushing and being interconnected by a crosspiece extending between two of the holes distally of the termination bushing.

In accordance with still a further mode of the invention, there is provided the step of attaching some of the tendons to a termination bushing at a distal end of the hollow body as steering tendons, attaching others of the tendons to one of the vertebrae as non-steering tendons, and steering the distal end with the steering tendons.

In accordance with still an added mode of the invention, there is provided the step of varying the number of the tendons along the hollow body for providing zones of varying stiffness.

In accordance with still an additional mode of the invention, there is provided the step of providing a greater number of the tendons toward a distal end than toward a proximal end of the hollow body, for increasing stiffness at the distal end.

In accordance with a concomitant mode of the invention, there is provided the step of cuffing at least one end of the corrugated tube to prevent vacuum leakage.

Other features which are considered as characteristic for the invention are set forth in the appended claims.

Although the invention is illustrated and described herein as embodied in a torque-transmitting, variably-flexible, corrugated insertion device and a method for transmitting torque and variably flexing a corrugated insertion device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 12A is an enlarged, perspective view of a U-shaped tendon;

DETAILED DESCRIPTION OF THE INVENTION

Figure 1:
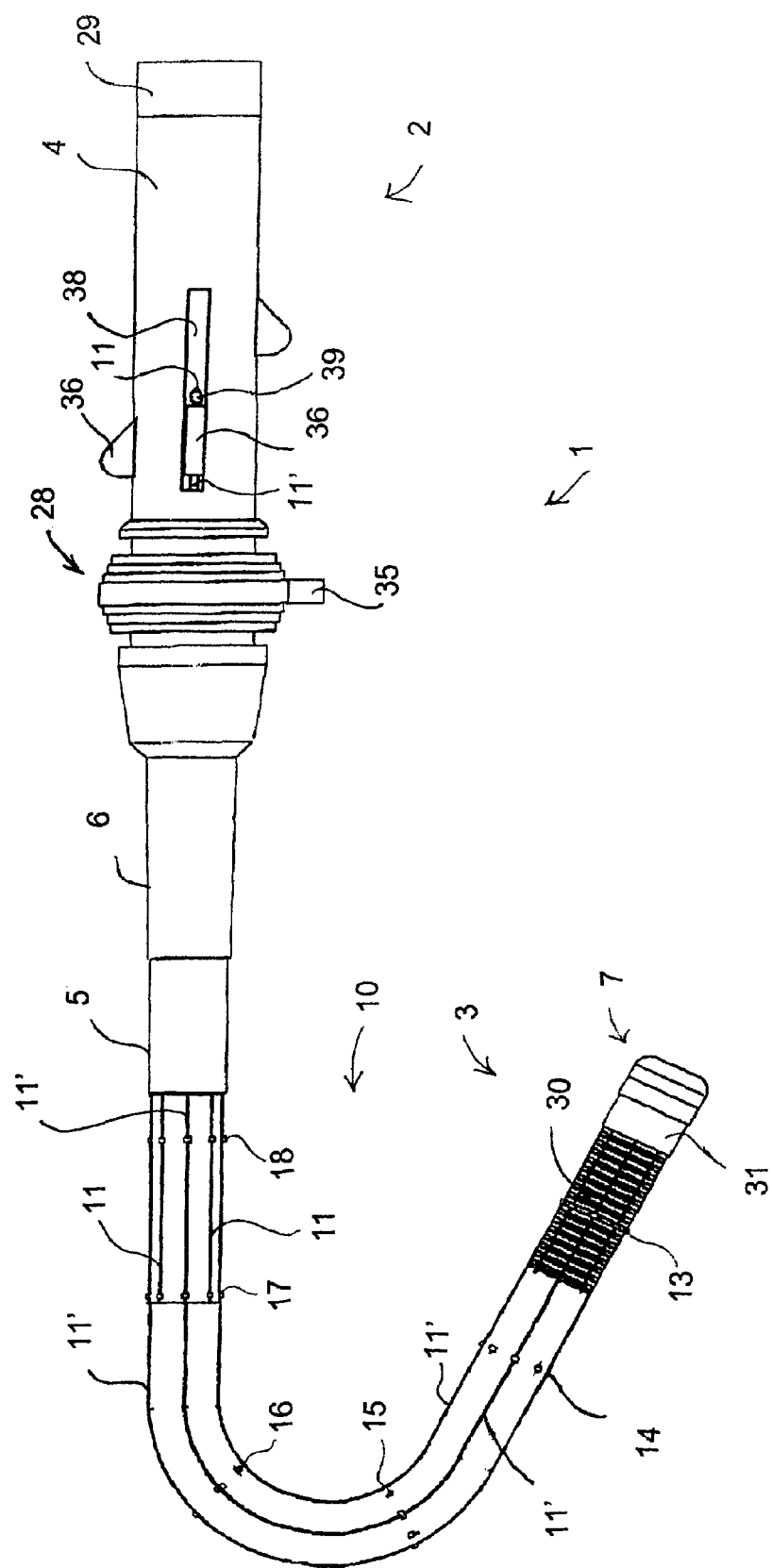
FIG. 1 is a diagrammatic, side-elevational view of a torque-transmitting, variably-flexible, corrugated insertion device according to the invention, in which an outer jacket has been partly removed to show corrugations, tendons and vertebrae and in which the device has been steered to the right.

Referring now to the figures of the drawings in detail and first, particularly, to FIG. 1 thereof, there is seen a torque-transmitting, variably-flexible, corrugated insertion device 1 according to the invention. The insertion device 1 has a hollow body with a proximal end 2 for manipulation by an operator and for receiving an instrument such as an endoscope or a colonoscopy. The insertion device 1 also has a distal end 3 for insertion into a patient and for protrusion of the instrument. A handle 4 of the hollow body for control by the operator is disposed at the proximal end 2. An outer jacket 5 of the hollow body extends to a tip 7, which may be formed of rubber, at the distal end 3, but only a portion of the outer jacket has been shown in order to illustrate other details of the device disposed within the outer jacket 5. A flexible strain relief retainer 6 is disposed between the handle 4 and the outer jacket 5. The outer jacket 5 and the flexible strain relief retainer 6 provide a flexible section with a given length extending beyond the handle 4. The handle 4 has a sliding valve 28 and a septum valve assembly 29, which will be explained in greater detail below with regard to FIG. 2. The handle 4 also has a vacuum connection or nipple 35 for controlling stiffness of the device, as will be explained below as well. A corrugated tube 30, which is only illustrated in the region of the distal tip 7, actually extends to the flexible strain relief retainer 6.

The insertion device 1 may be steerable or non-steerable. If the device is steerable, a steering assembly 10 is provided which includes six vertebrae 13-18 shown as being disposed along the hollow body. However, more or fewer vertebrae can be provided in dependence on the length, diameter and use of the hollow body. Eight tendons 11, 11' are equally spaced apart about the circumference of the hollow body between the vertebra 17 and the handle 4, although only five can be seen in FIG. 1. Four of the tendons which extend from a tendon termination bushing 31 at the tip 7 to the handle 4 are so-called steering tendons 11'. Other tendons which only extend between the vertebra 17 and the handle 4 are so-called non-steering tendons 11.

Each of the four steering tendons 11' is attached at its proximal end to a respective knob 36 which slides within a respective slot 38 in the handle 4. A stop 39 is also disposed on each tendon 11'. When a knob 36 is slid proximally, it pushes a stop 39 and pulls a tendon 11' to steer the hollow body. In the condition shown in FIG. 1, the knob 36 at the bottom has been slid proximally so that the tip 7 of the hollow body has been steered downward. If different knobs 36 are moved, the hollow body will be steered in different directions. When the knobs 36 are forced distally, the knobs can freely slide independently of the tendons 11' to prevent buckling of the tendons 11'. It will be readily understood that if two of the knobs are slid proximally, the tip 7 will move in a direction between the two directions that each one of the knobs would have moved the tip if moved individually.

Figure 2:
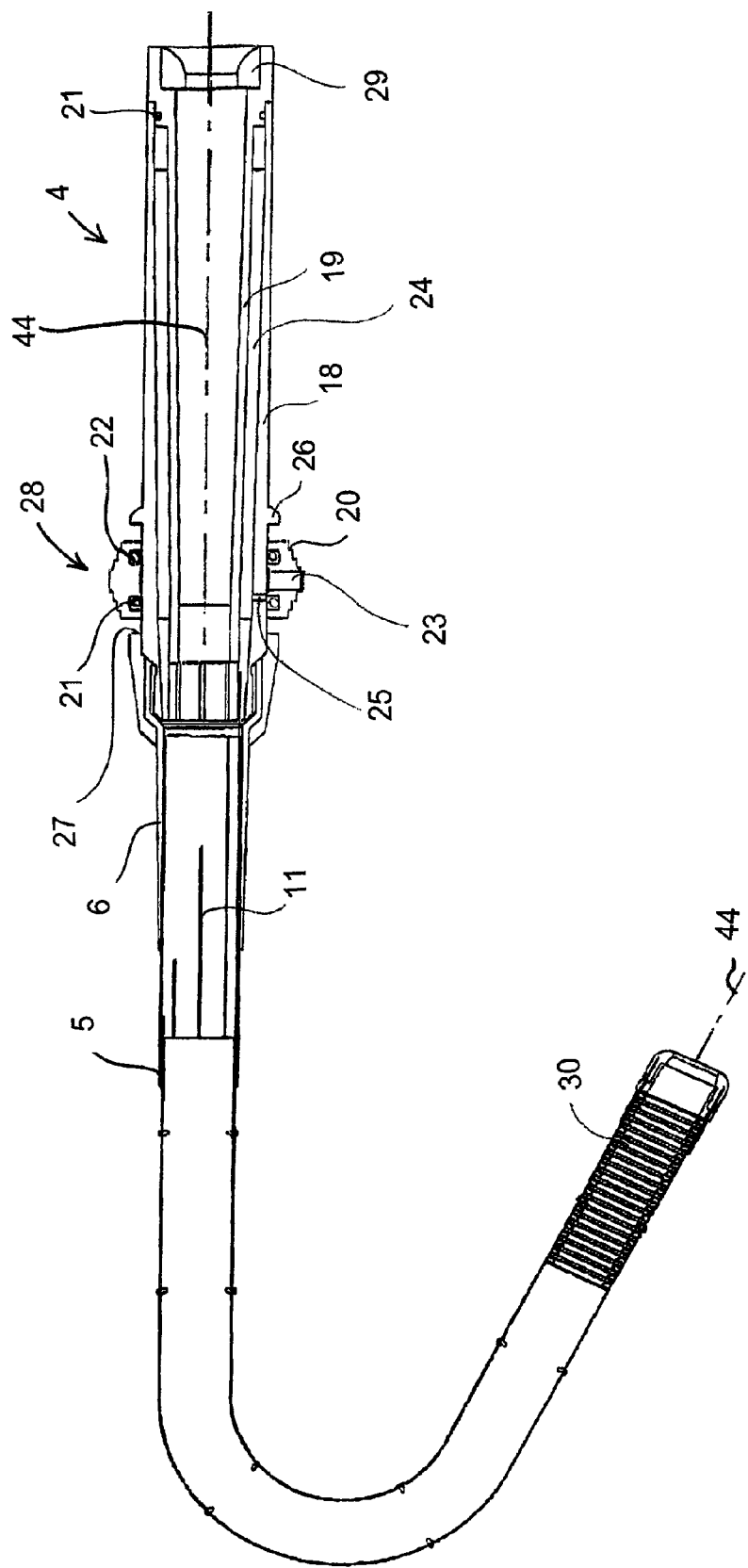
FIG. 2 is a side-elevational view of the insertion device in which corrugations are illustrated at the distal tip as in FIG. 1 and in which an outer covering of a handle has been removed.

In FIG. 2, an outer covering of the handle 4 has been removed to show details of the sliding valve 28 and the septum valve assembly 29. The handle 4 has an inner handle 19 disposed within an outer handle 18, defining an annular vacuum plenum volume 24 therebetween which extends in longitudinal direction of the handle 4. A vacuum inlet/outlet hole or port 25 is formed in the body of the outer handle 18 and communicates with the volume 24. A sliding so-called tire valve thumb grip 20 encircles the outer handle 18 and is sealed thereto by O-ring seals having O-rings 21 in recesses 22 in the grip 20. An O-ring seal is also disposed at the proximal end of the handle 4. The grip 20 also has a vacuum inlet/outlet 23 for the connection or nipple 35. When the grip 20 is slid toward an annular stop 26, the vacuum inlet/outlet 23 is not in alignment with the vacuum inlet/outlet hole 25. However, when the grip 20 is slid toward an annular stop 27, the vacuum inlet/outlet 23 and the vacuum inlet/outlet hole 25 are aligned, providing communication between the connection or nipple 35 and the volume 24. Therefore, during operation, the grip 20 is slid toward the stop 27 to apply vacuum to stiffen the hollow body or to vent the vacuum to the atmosphere or supply air at atmospheric pressure to make the hollow body flexible again. The grip 20 is slid toward the stop 26 to maintain the stiffened or flexible condition of the hollow body attained by vacuum or venting or air supply through the connection or nipple 35. The septum valve assembly 29 is in the form of an end cap which is inserted into the proximal end of the outer handle 18 and provides a so-called septum seal for insertion of an instrument 44, such as an endoscopy or a colonoscopy, represented by a dot-dash line. End caps with various sized openings may be used in dependence on the instrument being used. The instrument passes through the hollow body and emerges at the distal tip 7. A diaphragm seal is provided between the septum valve assembly 29 and the inner handle 19.

Figure 3:
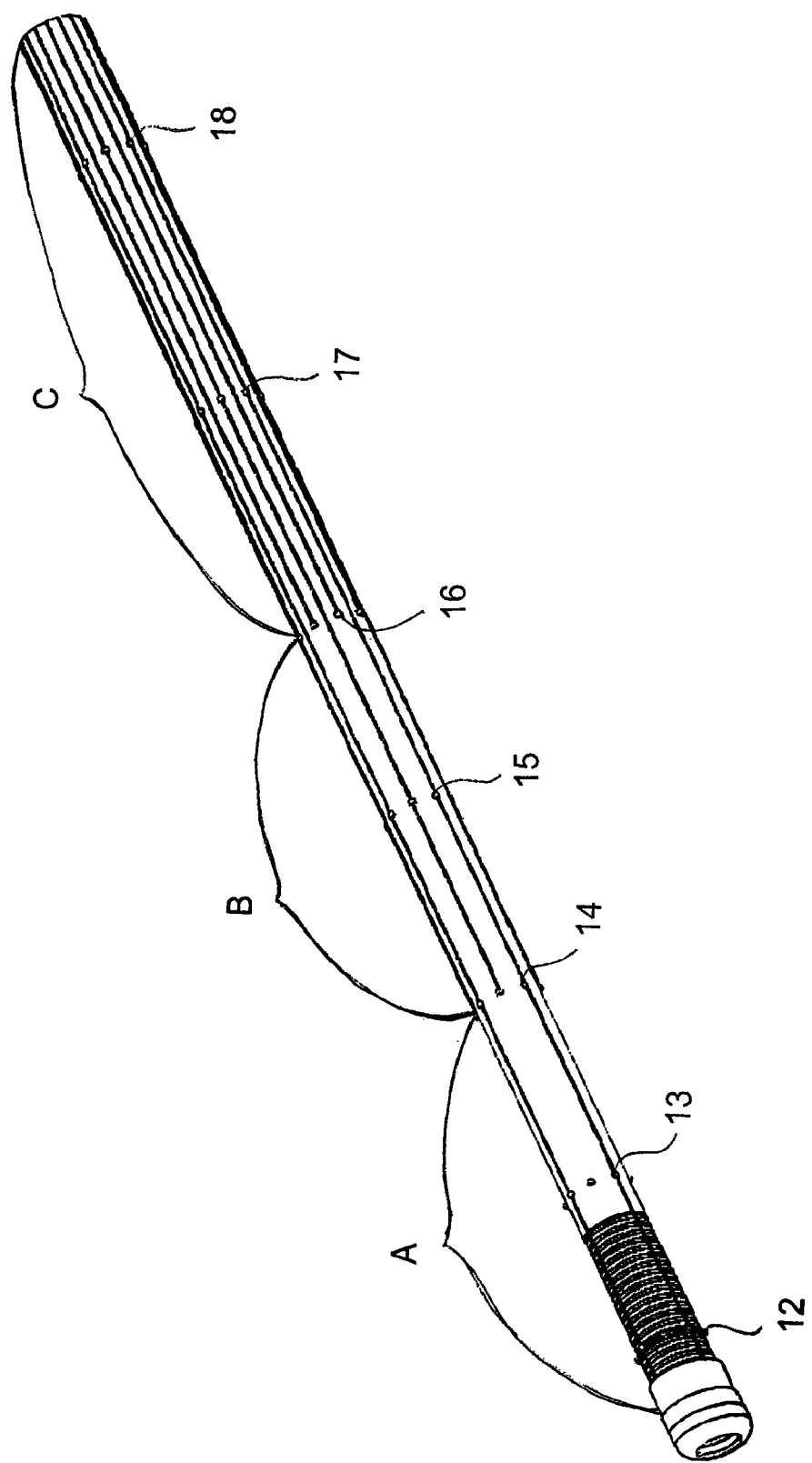
FIG. 3 is a perspective view showing stiffener zones of the insertion device and illustrating corrugations at the distal tip.

If the insertion device 1 is non-steerable, the number of tendons 11 may also be varied as shown in FIG. 3 to provide stiffness zones. For example, a stiffness zone A closest to the distal tip 7 has four tendons, a stiffness zone B has eight tendons and a stiffness zone C closest to the handle 4 has sixteen tendons. A zone with more tendons will be stiffer than a zone with fewer tendons. The number of tendons and their location within the zones as well as the number of zones can be increased or decreased, depending on the application of the device. Vertebrae 12-18, which in this case are seven in number, are also shown. The four tendons in the zone A all end at the termination bushing 31 but are free to slide elsewhere. Four of the eight tendons in zone B, which do not extend to zone A, are fixed at the vertebra 14 between zones A and B, which is therefore referred to as a termination vertebra, but are free to slide elsewhere. Similarly, eight of the sixteen tendons in zone C, which do not extend into zones A and B, are fixed at the termination vertebra 16 between zones B and C but are free to slide elsewhere.

Figure 4:
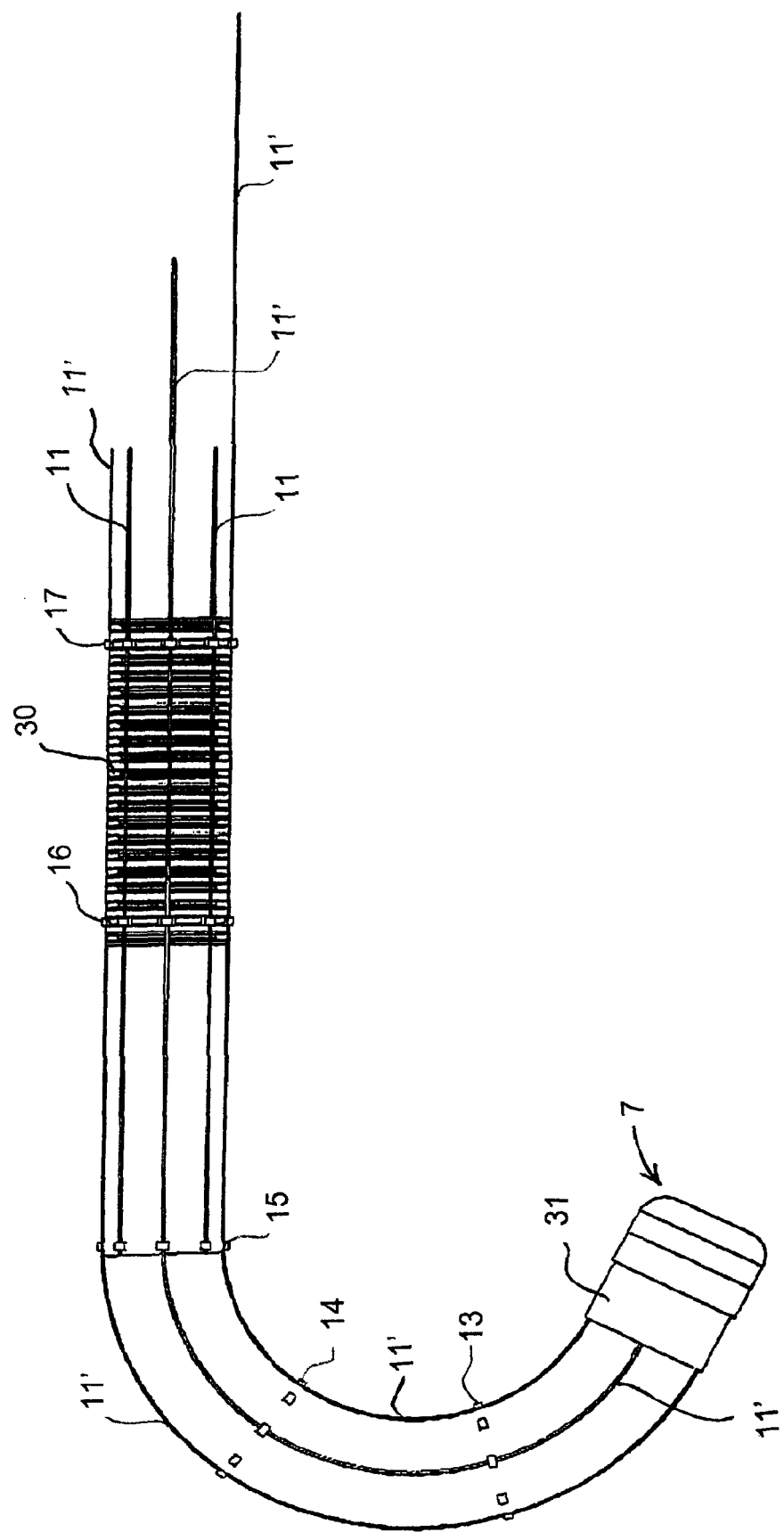
FIGS. 4 and 5 are fragmentary, side-elevational views of a steering assembly of the insertion device with corrugations illustrated in different locations.
Figure 5:
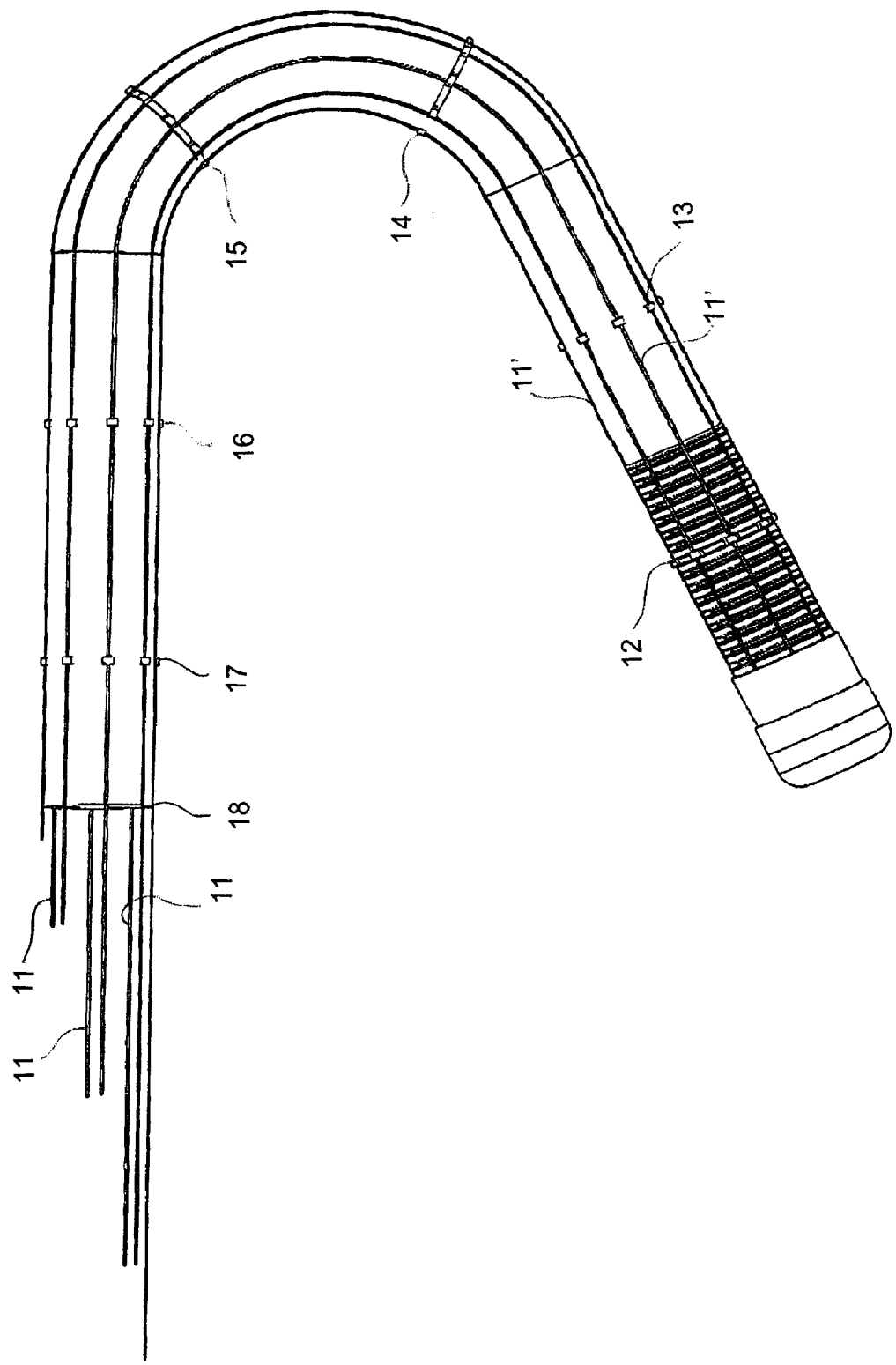

FIG. 4 shows the device 1 with the handle 4 removed, from which it can be seen that the four steering tendons 11' of the steering assembly 10 continue toward the handle from the tip 7, whereas the non-steering tendons 11 only run from the termination vertebra 15 to the handle. It is also seen that as the insertion device is steered, the steering tendons 11' on the outside of the bend become shorter and the steering tendons 11' on the inside of the bend become longer. FIG. 5 shows a similar view to FIG. 4, in which it can be seen how a greater number of vertebrae react to bending. In the case of FIG. 5, eight steering tendons 11' extend to the termination bushing 31, whereas six non-steering tendons 11 extend from the termination vertebra 18 to the handle.

Figure 6:
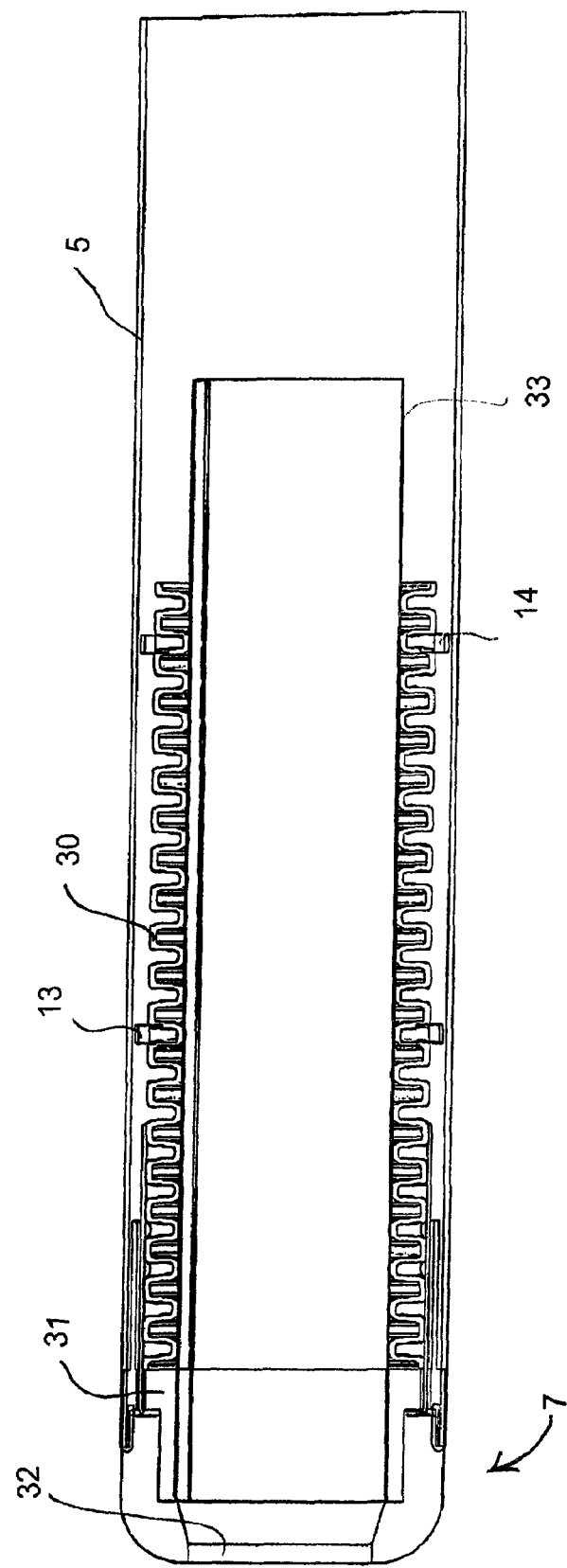
FIG. 6 is an enlarged, fragmentary, longitudinal-sectional view of a distal tip region of the insertion device.
Figure 7:
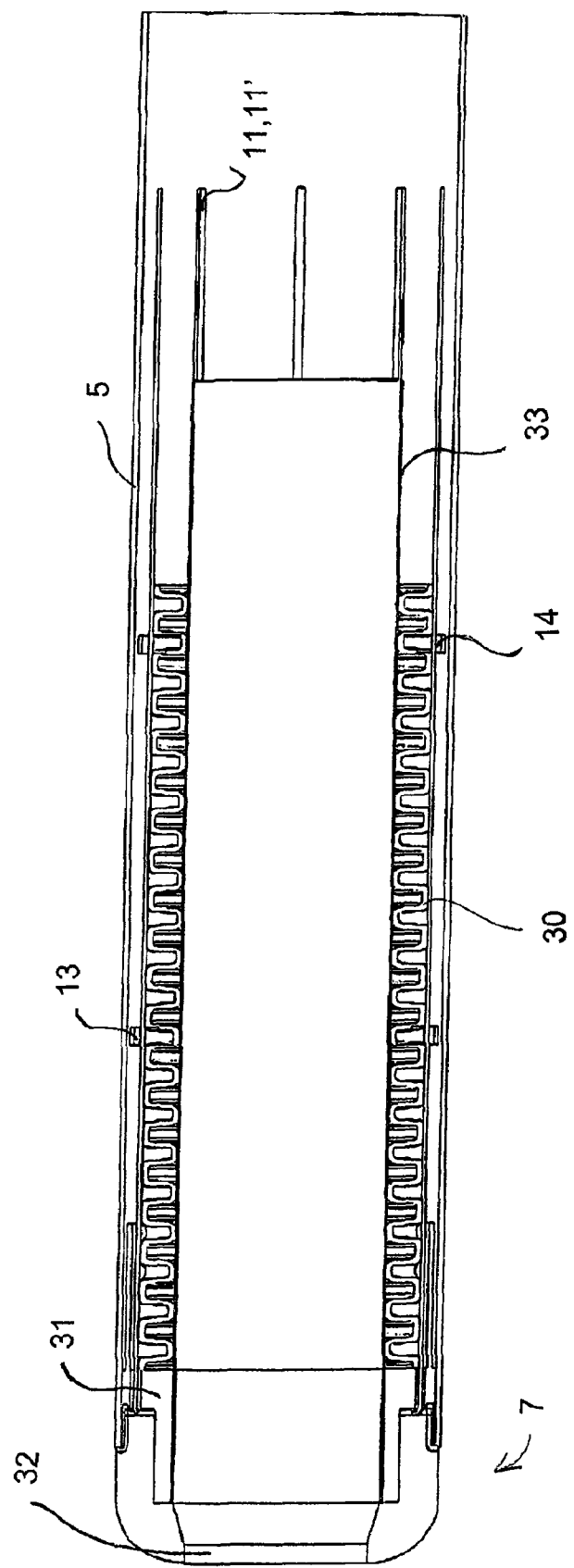
FIG. 7 is a view of the insertion device similar to FIG. 6, in which tendons have been shown.

In the enlarged view of FIG. 6, a portion of the corrugated tube 30 in the region of the tip 7 and the termination bushing 31 are shown. The tendons 11, 11', which have been omitted in FIG. 6 for the sake of clarity, are shown in FIG. 7 as extending through the vertebrae 13, 14 to the termination bushing 31. A tip restrictor 32 can also be seen at the tip 7. It may also be seen that an inner liner 33 extends within the corrugated tube 30. One purpose of the inner liner is to provide a surface on which the instrument will pass smoothly within the corrugated tube. The corrugated tube 30 may be formed of nylon or another suitable material. The inner liner 33 is made from a sheet of white plastic material which has an adhesive coating on one side. The inner liner 33 is rolled around an inflatable mandrel and heated in an oven, to form a bonded seam 42 (shown in FIGS. 11-13) and is sealed to an inner surface of the corrugated tube 30. The corrugations of the corrugated tube 30 have peaks and valleys. As viewed from within the corrugated tube 30, the inner liner 33 adheres to the peaks and extends somewhat into the valleys of the corrugations as dimples. Therefore, as the insertion device bends, the inner liner 33 stays tight along the corrugations on the outside of the bend and crinkles at the inside of the bend. The peaks and valleys of the corrugations also need not be of equal length along the length of the corrugated tube 30. For example, 70% of the length may be peaks and 30% valleys or 80% of the length may be peaks and 20% valleys. These variations will add to the adhesion of the inner liner to the corrugated tube and reduce the formation of dimples. However, a 50/50 corrugation ratio is shown in the figures. The outer jacket 5 may be formed of polyurethane or another suitable material which is similarly a flat sheet that is rolled and seamed. The outer jacket 5 and the inner liner 33 both extend to the termination bushing 31, which may be formed of polycarbonate.

Figure 8:
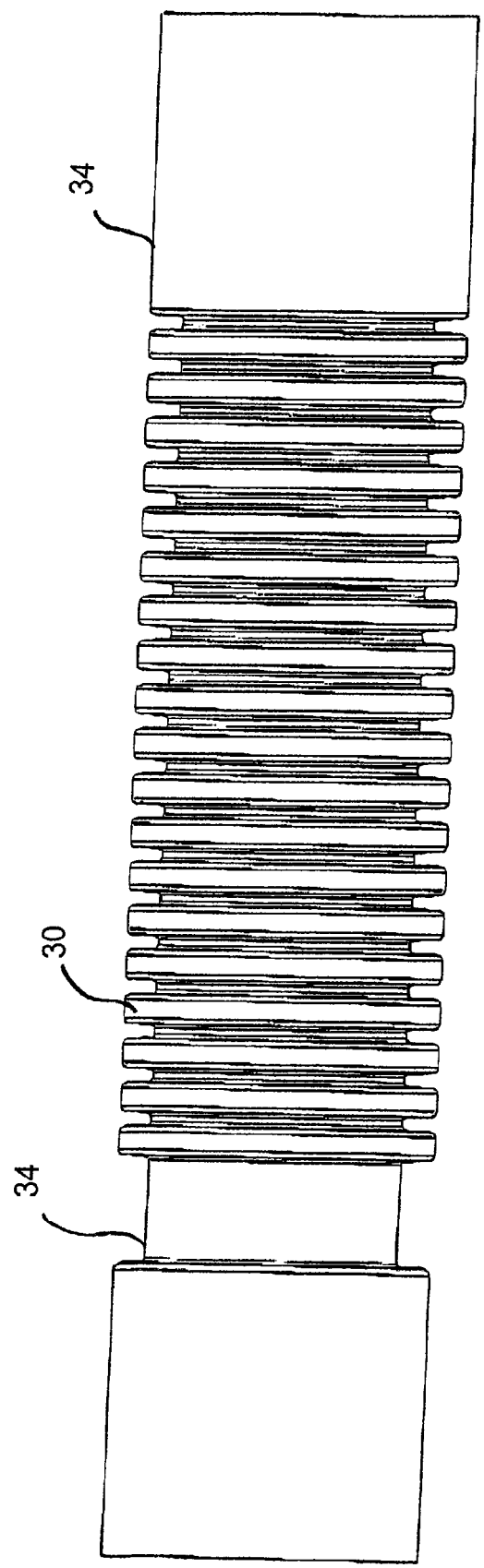
FIG. 8 is an elevational view of a corrugated tube of the insertion device in which straight and stepped cuffs have been shown.
Figure 9:
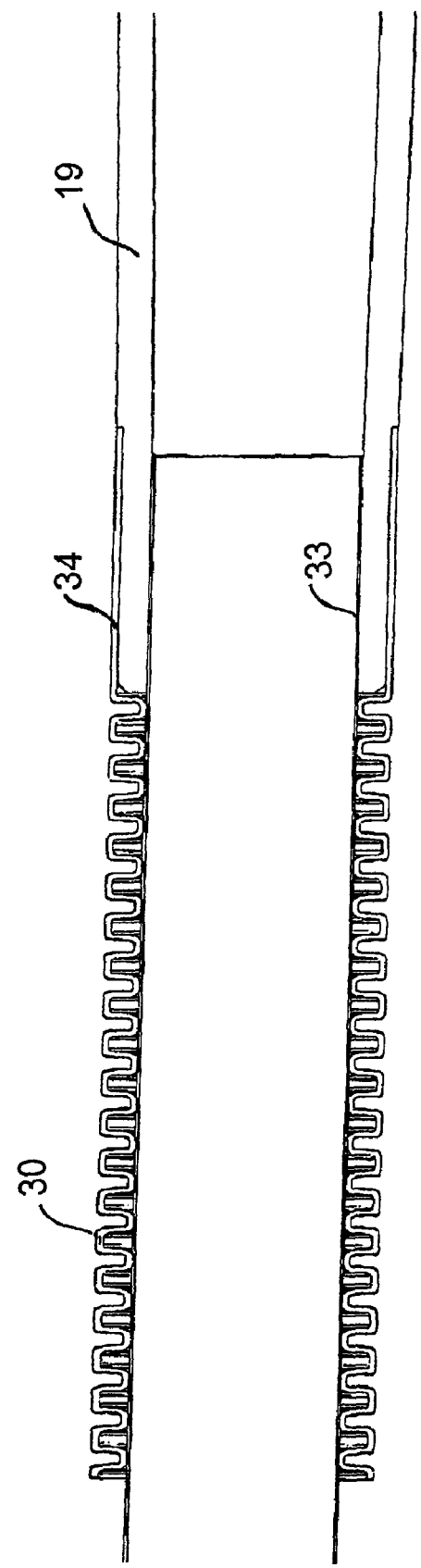
FIG. 9 is a fragmentary, longitudinal-sectional view of the insertion device in which an inner liner, an inner handle and a corrugation cuff have been shown.

The corrugated tube is cuffed in order to prevent leakage paths for the vacuum applied within the hollow body and to protect the material of the inner liner. FIG. 8 illustrates two types of molded corrugation cuffs 34, namely a straight cuff on the left and a stepped cuff on the right, of the figure, both with a 50/50 corrugation ratio. FIG. 9 shows the inner handle 19 which is attached to a corrugation cuff 34, as well as the inner liner 33 that is sealed to the corrugated tube 30 and to the inner handle 19 to prevent a vacuum leakage path.

Figure 10:
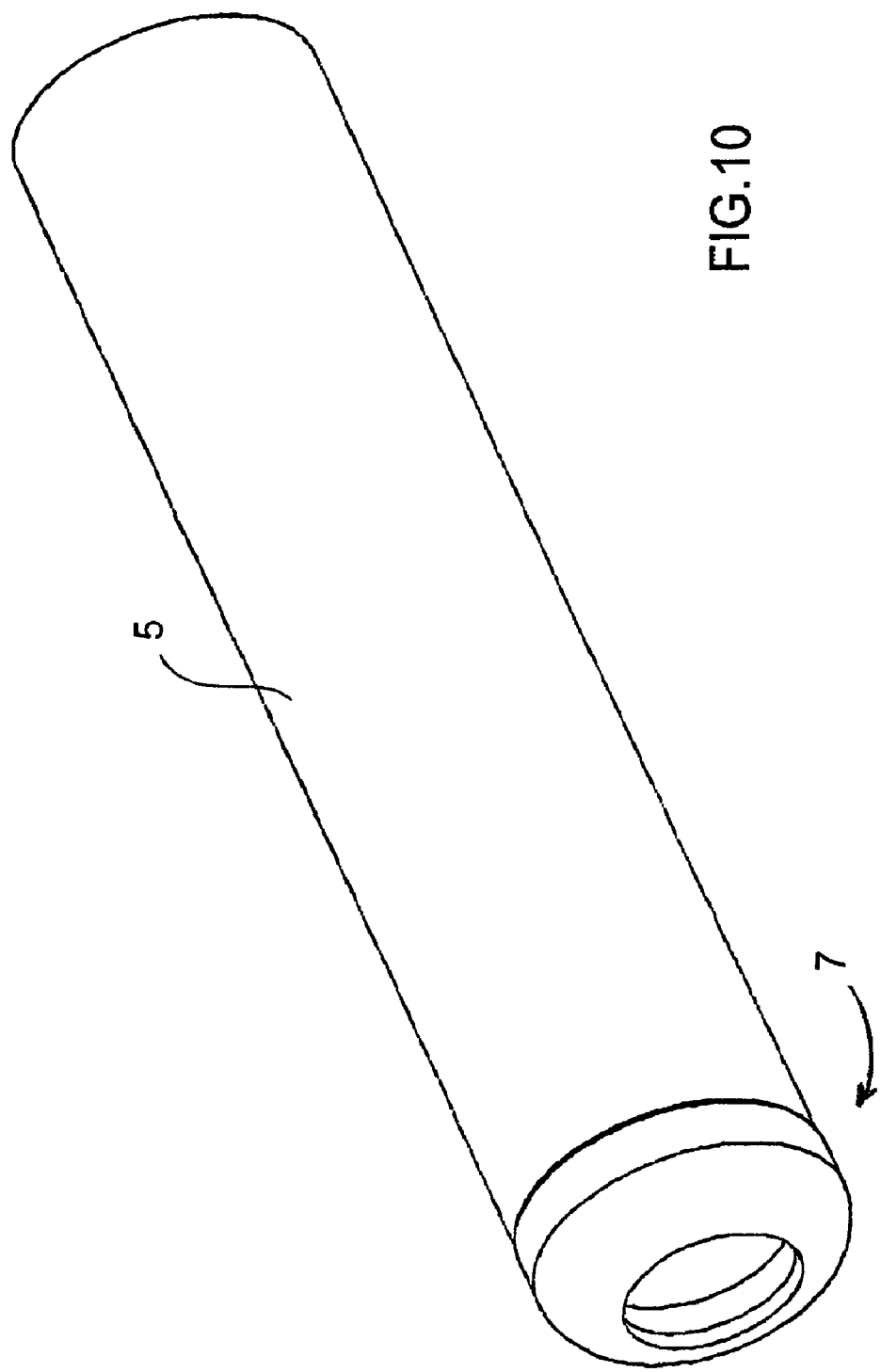
FIG. 10 is a fragmentary, perspective view of the distal tip region of the insertion device.

The perspective view of FIG. 10 illustrates the insertion device 1 in the region of the tip 7, including the outer jacket 5 extending to the tip, which is not shown in the other figures.

Figure 11:
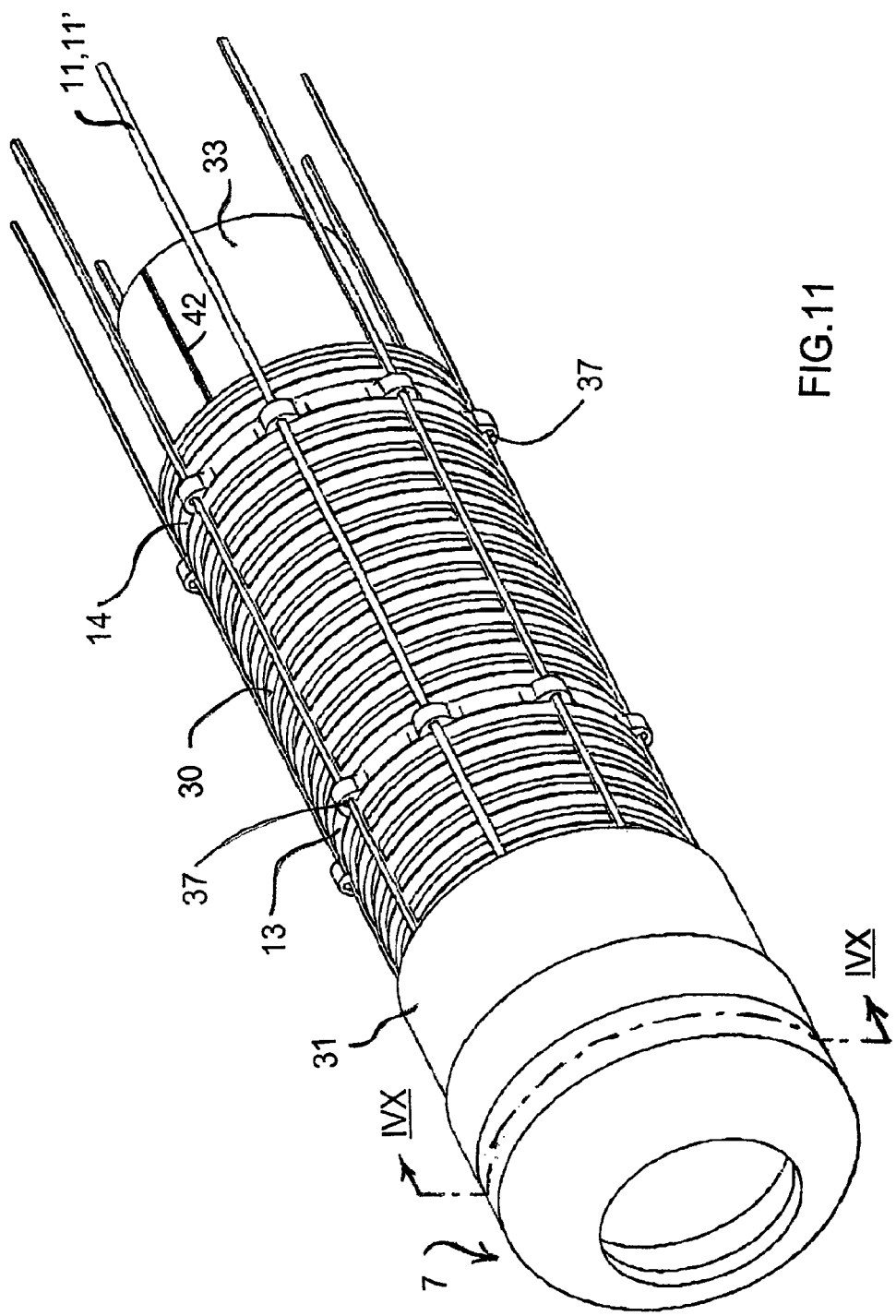
FIG. 11 is a fragmentary, perspective view of the distal tip region of the insertion device in which the outer jacket has been removed to show the tendons, the vertebrae and the corrugations.

The fragmentary, perspective view of FIG. 11 illustrates the insertion device 1 in the region of the tip 7, with the outer jacket removed to reveal the termination bushing 31 at the tip 7, the corrugated tube 30, the vertebrae 13, 14, the tendons 11 or 11' and the inner liner 33. It is seen that the tendons slide through channels 37 in the vertebrae.

Figure 12:
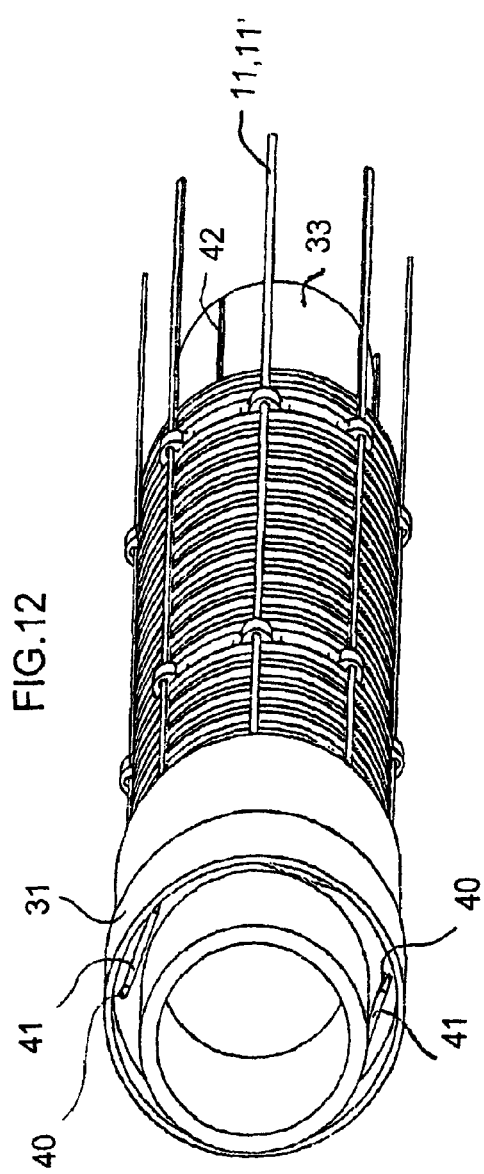
FIG. 12 is a view of the insertion device similar to FIG. 11, in which the tip has been removed.
Figure 12:
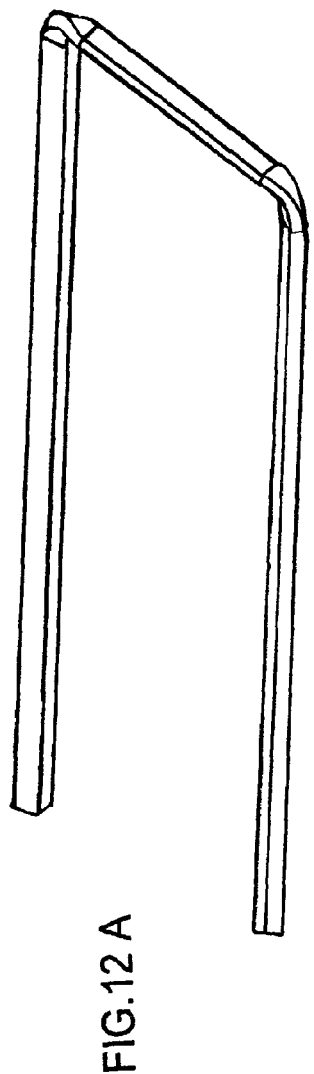

In FIG. 12, not only the outer jacket 5 but also the tip 7 have been removed to show how the tendons 11, 11' are anchored in the termination bushing 31. As can been seen, each tendon 11, 11' passes through a respective hole 40 in the termination bushing 31. Each two tendons together have a U-shape in the form of a large staple having a crosspiece 41 extending between two of the holes 40. This avoids the necessity of welding ends of tendons to a terminating vertebra or ring. The U-shaped tendons and crosspiece are best seen in FIG. 12A.

Figure 13:
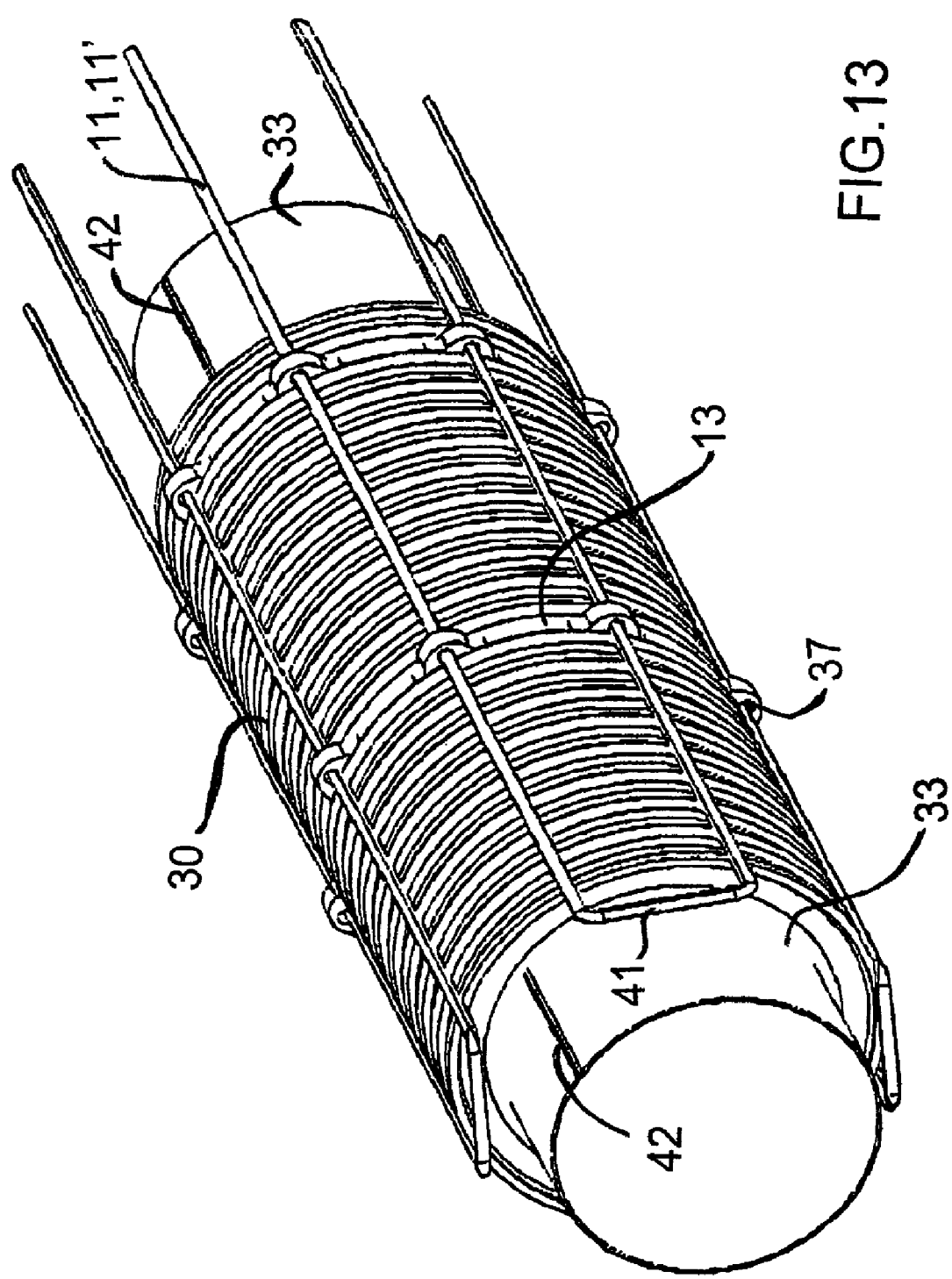
FIG. 13 is a view of the insertion device similar to FIGS. 11 and 12, in which the tip and a termination bushing have been removed.

In FIG. 13, not only the outer jacket 5 and the tip 7 but also the termination bushing 31 have been removed to show a portion of the inner liner 33 which is sealed on the inner surface of the termination bushing 31 for vacuum sealing and smooth movement of the instrument or scope 44. The crosspieces 41 of the tendons 11, 11' as well as the seam 42 of the inner liner are also clearly shown.

Figure 14:
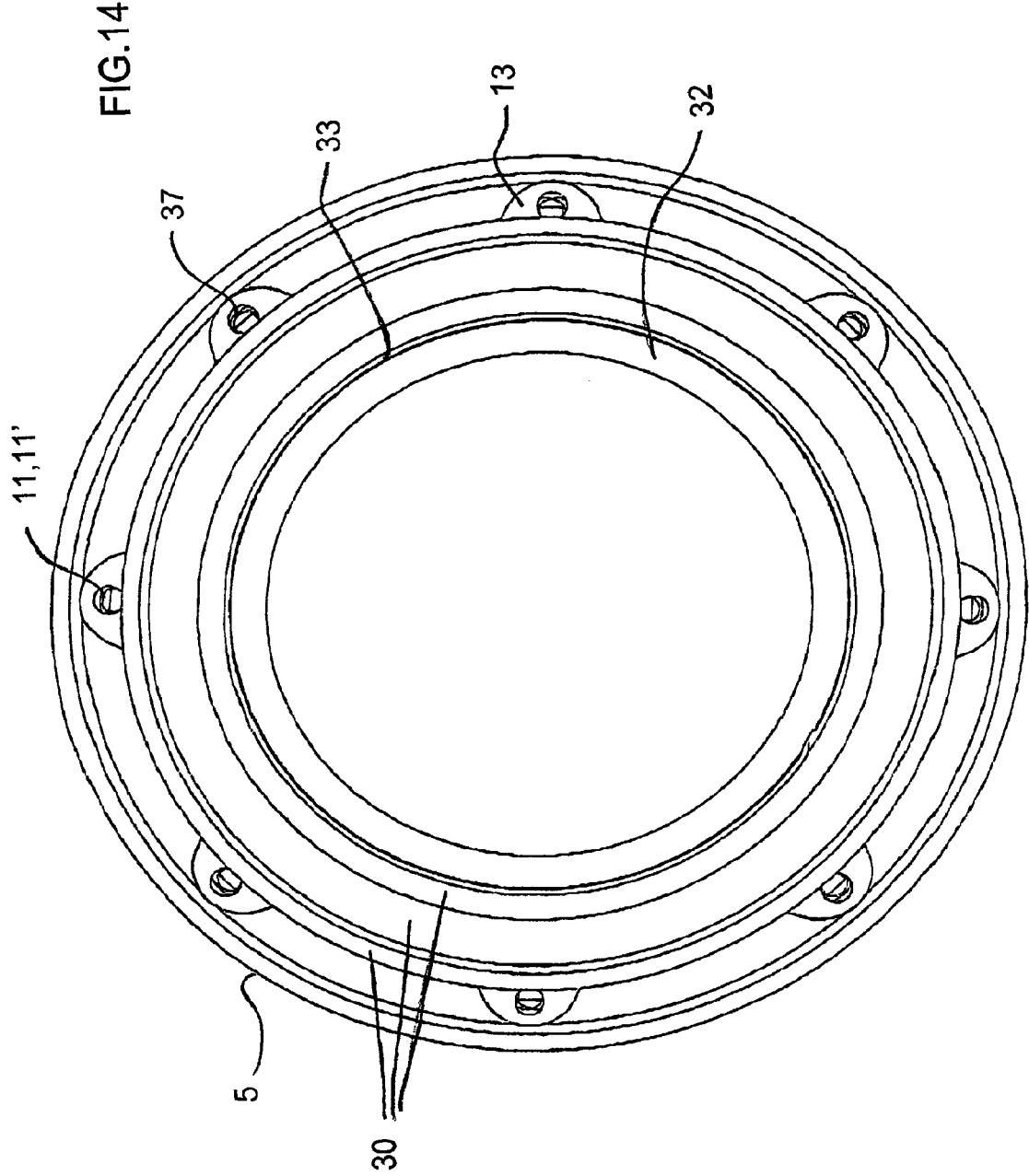
FIG. 14 is a cross-sectional view of the insertion device, which is taken along a line IVX-IVX of FIG. 11, in the direction of the arrows.

FIG. 14 is a cross-sectional view of the insertion device 1 which is taken through the flexible tip restrictor 32, as seen in the direction of the vertebra 13. Therefore, the outer jacket 5, the vertebra 13 with the tendons 11, 11', the corrugated tube 30 with the peaks and valleys and the tip restrictor 32, can be seen.

Figure 15:
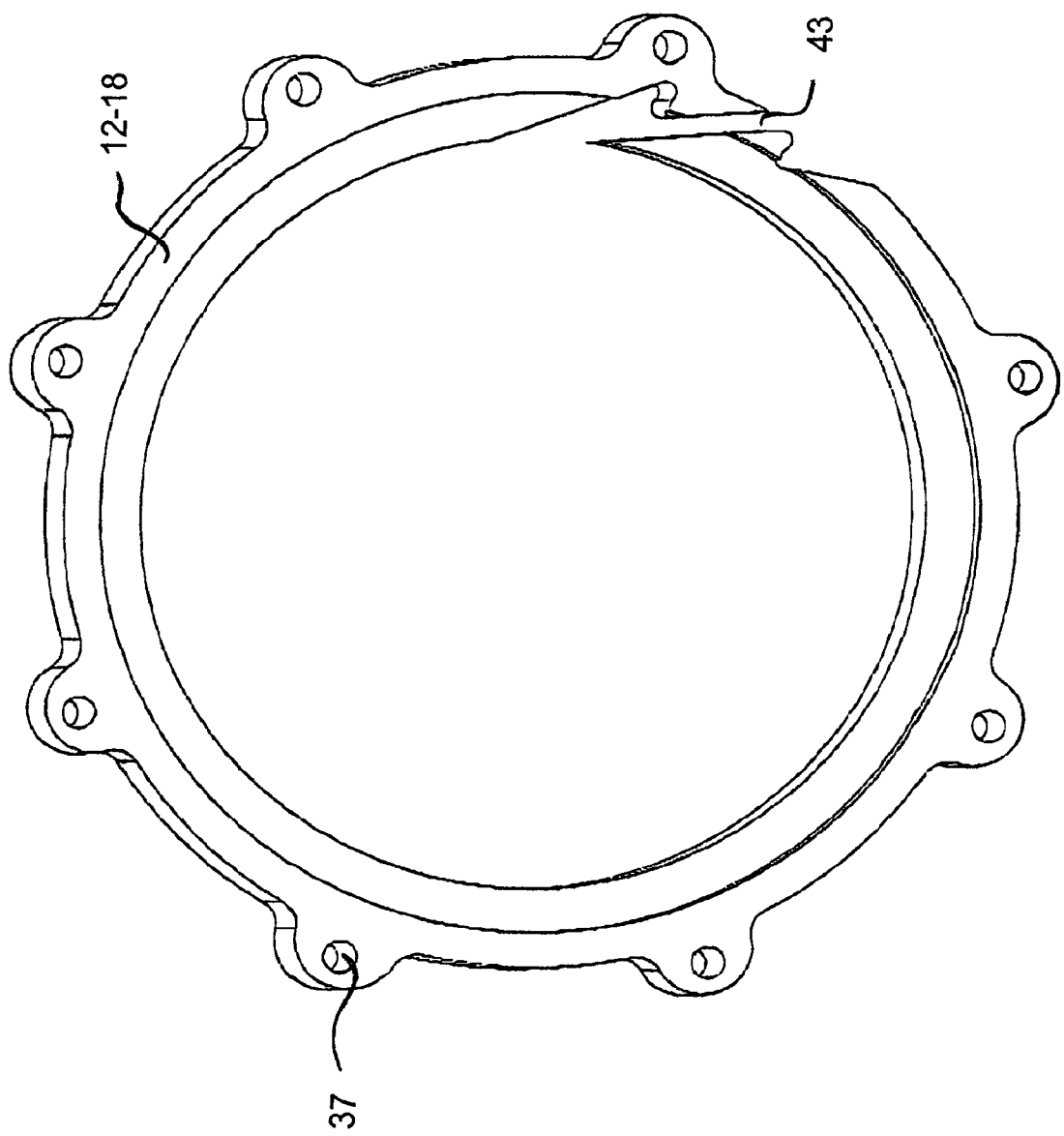
FIG. 15 is a further enlarged, perspective view of a snap vertebra of the insertion device.
Figure 16:
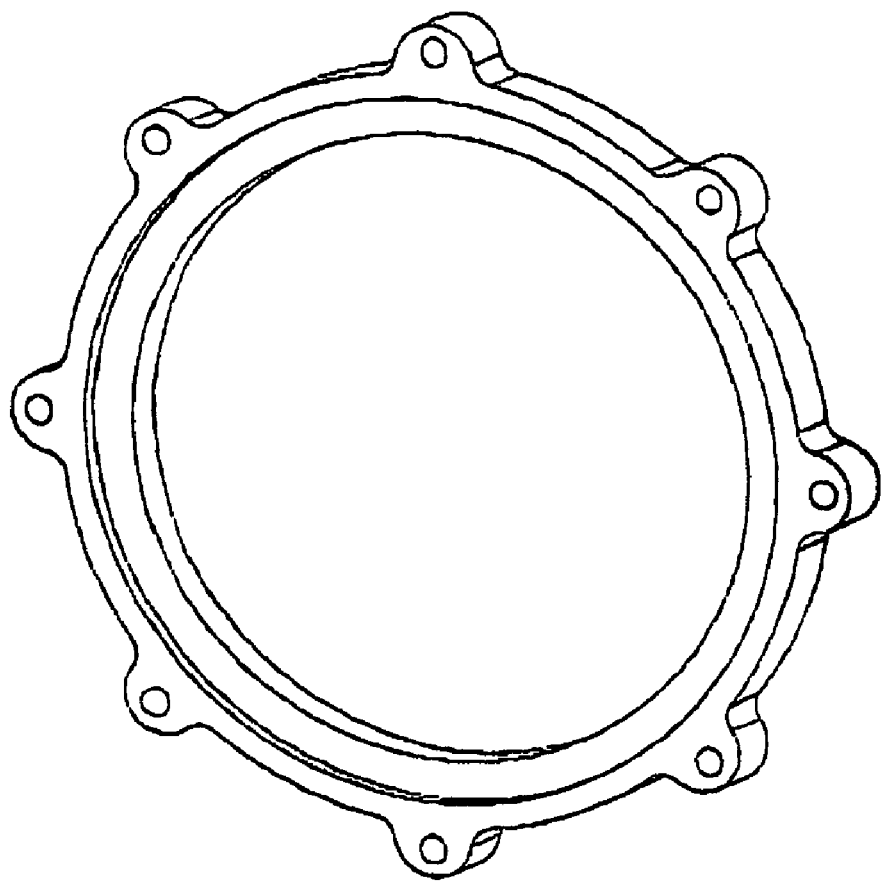
FIG. 16 is a perspective view of a continuous vertebra of the insertion device.

Representative vertebrae 12-18 are shown in FIGS. 15 and 16. The vertebra of FIG. 15 is a so-called latch ring constructed for snap installation. The vertebra is formed of elastic material which permits it to be expanded at a parting line and opened at a gap 43, so that it can be snapped over the corrugated tube 30 between two peaks thereof. Therefore, the vertebra can be installed at any location desired along the corrugated tube for support of the tendons. The vertebra shown in FIG. 16 is intended to be placed at an end of the corrugated tube 30, where no expansion and snapping into place are required.

The operation of the variably flexible insertion device 1 will now be described below by making reference to the above-described figures. If the steerable embodiment is used, the device 1 is flexed against the stiffness of the corrugated tube 30, for example upon traversing the rectosigmoid junction, by sliding one or more of the knobs 6. In either the steerable or non-steerable embodiment, if it is desired to maintain that flexed condition for guiding an endoscope, such as a colonoscopy, vacuum is applied at the connection or nipple 35. When suction is applied to create the vacuum, it causes the inner sleeve 33 and the outer jacket 5 to approach each other with the corrugated tube 30 and the tendons 11, 11' sandwiched and frictionally locked therebetween. Therefore, the vacuum connection or nipple 35 acts as a device for transitioning the hollow body 4, 7, 19, 5, 33, 30 between a relatively flexible condition and a relatively stiff condition through the application of a vacuum. As long as the vacuum is applied, the device 1 maintains its flexed condition. The positions of the knobs 6 in FIGS. 1, 2, 4 and 5 show that in the flexed condition, the tendons 11' at the outer periphery of the bend become shorter and the tendons 11' at the inner periphery of the bend become longer, since they are all fixed in place at the termination bushing 31.

The tendons or wires are passive elements which are not in tension at any time. The tendons float within the hollow body when it is in the flexible condition, except where they are fixed to termination vertebrae or the termination bushing 31 at the distal end. The tendons are frictionally locked by the inner sleeve 33 and the outer jacket 5 when the hollow body is in the stiff condition. However, in both the relatively flexible condition and the relatively stiff condition, the tendons have no active control imposed on them and are not pulled or constrained.

When it is desired to resume flexibility of the device 1, the vacuum is vented or replaced by air at ambient or positive pressure. This causes the inner sleeve 33 and the outer jacket 5 to release the tendons and allows the stiffness of the corrugated tube 30 to place the device 1 into its normally flexible condition.

The device is intended to be used in a manner similar to prior art devices. Therefore, the device will be placed over the endoscope. The endoscope will then be inserted into the rectum. The device will then be pushed in its flexible condition, to follow the curvature of the scope. The device will then be stiffened, allowing the scope to be pushed forward with less pressure exerted on the colon of the patient. This procedure can be repeated until the scope reaches the cecum.

An alternative use of the device is to aid in small bowel endoscopy. The device is placed over the endoscope. The endoscope is inserted into the patient transorally, through the stomach and then partially into the small bowel. The device is then pushed in its flexible condition, to follow the curvature of the scope. The device is then stiffened, allowing the scope to be pushed forward without the scope looping in the stomach.

Another use of the device is for aiding in access to internal body parts, such as the gallbladder, through an opening of an internal body cavity, such as the stomach. The device is placed over the endoscope. The endoscope is inserted into the patient transorally, through the stomach and then up against the internal surface of the stomach. The device is then pushed in its flexible condition, to follow the curvature of the scope. The device is then stiffened, allowing the surgeon to create an opening in the stomach wall without the scope looping in the stomach. Once the opening is created, the device and the scope can be advanced outside the stomach. The device can then be stiffened to create a stable platform to perform surgical procedures outside of the stomach. The device could contain one or more features (i.e. balloons) for sealing the outer periphery of the device to the stomach wall to prevent gastric fluids from exiting the stomach.

In each of these procedures described above, the knobs and tendons are used to steer the insertion device within the body as needed, while the corrugated tube allows the device to be twisted as needed.

What is claimed is:

1. A method for transmitting torque and variably flexing an insertion device for receiving an instrument, the method comprising the following steps:
    providing a hollow body;
    transmitting torque along the hollow body with a corrugated tube;
    applying suction to create a vacuum in the hollow body for placing the hollow body in a relatively stiff condition;
    relieving the vacuum for placing the hollow body in a relatively flexible condition;
    maintaining the hollow body in the relatively flexible and relatively stiff conditions with tendons disposed within the hollow body, the vacuum created by the applied suction frictionally locking the tendons and the corrugated tube in place in the relatively stiff condition; and
    individually adjusting at least some of the tendons in length for steering a distal end of the hollow body.

2. The method according to claim 1, which further comprises preventing vacuum leakage and aiding in insertion of the instrument with a liner disposed within the corrugated tube.

3. The method according to claim 2, which further comprises adhesively connecting the liner to the corrugated tube.

4. The method according to claim 1, which further comprises carrying out the step of individually adjusting at least some of the tendons as steering tendons with knobs each connected to a respective one of the steering tendons and each sliding in a respective slot formed in a handle at a proximal end of the hollow body.

5. The method according to claim 1, which further comprises providing the hollow body with an outer jacket and an inner sleeve, providing the tendons at least partly between the outer jacket and the inner sleeve, providing the corrugated tube between the outer jacket and the inner sleeve, and carrying out the step of applying suction between the outer jacket and the inner sleeve with a transitioning device for frictionally locking the tendons and the corrugated tube in place.

6. The method according to claim 5, which further comprises providing a vacuum connection as the transitioning device, and actuating the vacuum connection with a valve at a handle of the hollow body.

7. The method according to claim 1, which further comprises guiding the tendons with vertebrae disposed along the corrugated tube.

8. The method according to claim 7, which further comprises placing the vertebrae between corrugation peaks of the corrugated tube for guiding the tendons.

9. The method according to claim 8, which further comprises snapping the vertebrae onto the corrugated tube by elastically opening the vertebrae at a parting line into a gap.

10. The method according to claim 7, which further comprises permitting movement of at least some of the tendons through channels formed in at least some of the vertebrae.

11. The method according to claim 1, which further comprises attaching at least some of the tendons to a termination bushing at a distal end of the hollow body.

12. The method according to claim 11, which further comprises forming each two of the tendons into legs of a U-shaped configuration passing through holes in the termination bushing and being interconnected by a crosspiece extending between two of the holes distally of the termination bushing.

13. The method according to claim 7, which further comprises attaching some of the tendons to a termination bushing at a distal end of the hollow body as steering tendons, attaching others of the tendons to one of the vertebrae as non-steering tendons, and steering the distal end with the steering tendons.

14. The method according to claim 1, which further comprises varying the number of the tendons along the hollow body for providing zones of varying stiffness.

15. The method according to claim 14, which further comprises providing a greater number of the tendons toward a distal end than toward a proximal end of the hollow body, for increasing stiffness at the distal end.

16. The method according to claim 2, which further comprises cuffing at least one end of the corrugated tube to prevent vacuum leakage.

* * * * *